United States Patent
Wadström et al.

(10) Patent No.: US 6,262,316 B1
(45) Date of Patent: *Jul. 17, 2001

(54) **ORAL PREPARATION FOR THE PROPHYLACTIC AND THERAPEUTIC TREATMENT OF *HELICOBACTER SP.* INFECTION**

(75) Inventors: Torkel Wadström; Pär Alejung, both of Lund (SE)

(73) Assignee: Astacarotene AB, Gustavsberg (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/367,838

(22) PCT Filed: Feb. 5, 1998

(86) PCT No.: PCT/EP98/00628

§ 371 Date: Jan. 21, 2000

§ 102(e) Date: Jan. 21, 2000

(87) PCT Pub. No.: WO98/37874

PCT Pub. Date: Sep. 3, 1998

(30) Foreign Application Priority Data

Feb. 27, 1997 (SE) .................................................... 9700708

(51) Int. Cl.[7] ........................... C07C 35/08; C07C 35/21; A61K 47/00; A61K 9/20
(52) U.S. Cl. ........................... 568/834; 568/832; 568/816; 424/439; 424/464
(58) Field of Search ............................ 414/439; 568/816, 568/832, 834

(56) References Cited

FOREIGN PATENT DOCUMENTS

| 07 099 924 | 4/1995 | (JP) . |
| 07 300 421 | 11/1995 | (JP) . |
| WO 95 00130 | 1/1995 | (WO) . |
| WO 96 23489 | 8/1996 | (WO) . |

OTHER PUBLICATIONS

Database WPI, Week 9603, Derwent Publications Ltd., London, GB AN 96–026969 XP002067981 (JP 07 300 421 AA, Nov. 14, 1995).

Database WPI, Week 9524, Derwent Publications Ltd., London, GB; AN 95–182023 XP002067980; (JP 07 099 924 A, Apr. 18, 1995).

P. Bubrick, "Production of Astaxanthin from Haematococcus", Bioresource Technology, vol. 38, 1991, pp. 237–239.

D. Bagchi et al., "Production of Reactive Oxygen species By Gastric Cells in Association with *Helicobacter Pylori*" Free Redical Research, vol., 24, No. 6, 1996, Amsterdame, NL, pp. 439–450.

*Primary Examiner*—Thurman K. Page
*Assistant Examiner*—Amy E Pulliam
(74) *Attorney, Agent, or Firm*—Bacon & Thomas

(57) ABSTRACT

An oral preparation for the prophylactic and/or therapeutic treatment of inflammation in the mucous membrane of mammalian gastrointestinal tract (especially the human stomach) caused by Hicobacter sp. (especially *H. pylori*) infection is described. The preparation comprises a prophylactically and/or therapeutically effective amount of at least one type of xanthophylles. The most preferred xanthophyll is astaxanthin which is soluble in oil, preferably naturally produced astaxanthin which is esterified with fatty acids. The oral preparation may further comprise carbohydrate structures, such as those which derive from the cell wall of the production alga Haematococcus sp. The preparation may also comprise a prophylactically and/or therapeutically effective amount of a water soluble antioxidant, such as ascorbic acid (vitamin C). The oral preparation is presented in a separate unit dose or in mixture with food.

26 Claims, No Drawings

ORAL PREPARATION FOR THE PROPHYLACTIC AND THERAPEUTIC TREATMENT OF *HELICOBACTER SP.* INFECTION

The present invention relates to an oral preparation for the prophylactic and/or therapeutic treatment of inflammation in the mucous membrane of mammalian gastrointestinal tract caused by Helicobacter sp. infection. The preparation comprises at least one type of xanthophylles, preferably naturally produced astaxanthin.

BACKGROUND OF THE INVENTION

Since a few years *Helicobacter pylon* is classified as a primary cause of type B gastritis in humans.

Various Helicobacter sp. infect different animals, and must penetrate the gastric surface mucous layer [O'Toole PW et al., Mol Microbiol 1994, 14:691–703] to colonize the gastric epithelium and sub-mucosa [Wadström T et al., Aliment Pharmacol Ther 1996, 10(suppl 1): 17–28.; Valkonen K H et al., Infect immun 1994, 62:3640–3648.; Moran A P et al., J Appi Bacteriol 1993, 75:184–189.; Wadström T et al., Eur J Gastroenterol Hepatol 1993, 5 (suppl 2):512–515]. Helicobacter is a flagellated motile organism probably penetrating the gastric mucous layer rapidly and efficiently with spiral movements associated with the unique spiral shape of this pathogen (Helicobacter from helix, which is Latin for spiral).

*Helicobacter pylori* can cause drastic changes of the gastric mucous membrane barrier functions in an early infection (i.e. type B gastritis) with breakdown of the hydrophobic lining of the gastric epithelium. This can cause back-flow of acid and pepsin from the lumen into the mucosa to cause peptic ulcers in the stomach and duodenum. It seems likely that this breakdown of the mucosa barrier also affects the uptake in the gastric mucosa of a number of substances in food such as certain food-associated carcinogens.

Xanthophylles, including astaxanthin, is a large group of carotenoids containing oxygen in the molecule in addition to carbon and hydrogen. The carotenoids are produced de novo by plants, fungi and some bacteria [Johnson E. A. and Schroeder W. A., 1995, Adv In Biochem Engin. Biotechn. 53: 119–178]. In biological tests astaxanthin has been shown to possess clearly the best antioxidative properties compared to other carotenoids [Miki W., 1991, Pure and Appl Chem 63 (1): 141–146].

At present, the therapeutic treatment of inflammation in the mucous membranes of mammalian gastrointestinal tract caused by Helicobacter sp. infection, mainly involves the use of so-called proton pump inhibitors, such as Losec® (omeprazol), and in case of gastric ulcers different antibiotics (which may cause the development of resistant strains).

DESCRIPTION OF THE INVENTION

The present invention provides an oral preparation for the prophylactic and/or therapeutic treatment of inflammation in the mucous membrane of mammalian gastrointestinal tract caused by Helicobacter sp. infection, which comprises a prophylactically and/or therapeutically effective amount of at least one type of xanthophylles.

The oral preparation according to the invention may comprise a mixture of different types of xanthophylles or different forms of the same xanthophyll, such as a mixture of synthetic astaxanthin and naturally produced astaxanthin.

In a particular embodiment of the invention the mammalian gastrointestinal tract is the human stomach, and the Helicobacter sp. is *H. pylori*.

The mechanism of the prophylactic and therapeutic effect of the xanthophylles in the treatment of inflammation in the mucous membrane of the mammalian gastrointestinal tract caused by Helicobacter sp. infection is not known, but it is believed that the antioxidative properties of the xanthophylies, which are soluble in fat/oil, play an important role in the protection of the hydrophobic lining of the mucous membrane so that Heilcobacter sp. cannot colonize.

In a preferred embodiment of the invention, the xanthophyll is dissolved in an oil of food grade.

In another preferred embodiment the type of xanthophyll is astaxanthin, particularly astaxanthin in a form esterified with fatty acids.

In yet another preferred embodiment the astaxanthin derives from a natural source, particularly a culture of the alga Haematococcus sp. [Renström B. et al, 1981, Phytochem 20(11) :2561–2564].

The oral preparation according to the invention may further comprise carbohydrate structures, such as lipopolysaccharides, polysaccharides and glycoproteins.

At present, the most preferred embodiment of the invention comprises algal meal having astaxanthin in esterified form with fatty acids dissolved in small droplets of naturally occurring oil and naturally occurring carbohydrate structures in the partially disrupted cell walls.

The oral preparation of the invention may comprise additional ingredients which are pharmacologically acceptable inactive or active in prophylactic and/or therapeutic use, such as flavoring agents, and a prophylactically and/or therapeutically effective amount of a water soluble antioxidant, especially ascorbic acid (vitamin C).

The oral preparation is presented in a separate unit dose or in mixture with food. Examples of separate unit doses are tablets, gelatin capsules and predetermined amounts of solutions, e. g. oil solutions, or emulsions, e.g. water-in- oil or oil-in-water emulsions. Examples of foods in which the preparation of the invention may be incorporated is dairy products, such as yoghurt, chocolate and cereals.

Another aspect of the invention is directed to a method of prophylactic and/or therapeutic treatment of inflammation in the mucous membrane of mammalian gastrointestinal tract caused by Helicobactersp. infection, which comprises administration to said mammal of an oral preparation according to the invention.

The daily dosis of the active ingredient of the invention will normally be in the range of 0.01 to 10 mg per kg body weight for a human calculated on the amount of astaxanthin, but the actual dosis will depend on the mammalian species and the individual species-specific biological effect.

EXPERIMENTS

The oral preparation used in the experiments is the xanthophyll astaxanthin which is commercially produced via culturing of the algae Haematococcus sp. by AstaCarotene AB, Gustavsberg, Sweden.

Astaxanthin from other sources, and other xanthophylles as well, are expected to be similarly useful for the purposes of the invention. An advantage of using astaxanthin from algae is, however, that the astaxanthin exists in a form esterified with fatty acids [Renström B. et al, ibid], which esterified astaxanthin thereby is more stable during handling and storage than free astaxanthin.

The naturally produced astaxanthin can be obtained also from fungi and crustaceans, in addition to from algae [Johnson E. A. and Schroeder W. A., ibid].

Fifty 6–8 weeks old Balb/cA mice weighing 28–30 g were infected with *H. pylori* by administration of $10^8$ cfu in phosphate buffer through a gastric tube into the stomach. The treatment was repeated three times on one-day intervals [Aleljung P., et al., 1996, FEMS Immunol Med Microbiol. 13: 303–309].

After 14 days, 10 mice were sacrificed and cultures were made on stomach biopsies to isolate *H. pylori*. The culturing takes seven days.

Twenty-one days after the infection with *H. pylori* half of the remaining animals were given feed supplemented by algal meal corresponding to 0.3 mg astaxanthin per animal per day for a period of 10 days.

On day 30 half of the animals in each group were sacrificed and culturing was made in a similar way as disclosed above.

On day 40 the rest of the animals were sacrificed and culturing was made in a similar way as disclosed above.

The results are given in Table 1.

TABLE 1

| The number of animals positive for *H. pylori* per number of sacrificed animals. | | |
|---|---|---|
| Day | Treated animals | Control animals |
| 14 | — | 8/10 |
| 30 | 0/8 | 8/10 |
| 40 | 0/10 | 7/10 |

From the results in Table 1 it is evident that the algal meal containing astaxanthin has a therapeutic effect and can be used for prophylactic purposes.

What is claimed is:

1. A method of therapeutic treatment of Helicobacter sp. infection in the mammalian gastrointestinal tract, which comprises oral administration to said mammal of a therapeutically effective amount of an oral preparation comprising at least one type of xanthophylles.

2. The method according to claim 1, wherein the type of xanthophyll is astaxanthin.

3. The method according to claim 2, wherein the mammalian gastrointestinal tract is the human stomach and the Helicobacter sp. is *H. pylori*.

4. The method according to claim 2, wherein the xanthophyll is dissolved in an oil of food grade.

5. The method according to claim 2, wherein the astaxanthin is in a form esterified with fatty acids.

6. The method according to claim 5, wherein the astaxanthin derives from a natural source.

7. The method according to claim 6, wherein the natural source is a culture of the alga Haematococcus sp.

8. The method according to claim 2, wherein the oral preparation further comprises carbohydrate structures.

9. The method according to claim 8, wherein the oral preparation comprises algal meal having astaxanthin in esterified form with fatty acids dissolved in small droplets of naturally occurring oil and naturally occurring carbohydrate structures in the partially disrupted algal cell walls.

10. The method according to claim 2, which further comprises administration of a therapeutically effective amount of a water soluble antioxidant.

11. The method according to claim 10, wherein the water soluble antioxidant is ascorbic acid (Vitamin C).

12. The method according to claim 2, wherein the oral preparation is presented in a separate unit dose or in mixture with food.

13. Method of prophylactic treatment of Helicobacter sp. infection in the mammalian gastrointestinal tract, which comprises oral administration to said mammal of a prophylactically effective amount of an oral preparation comprising at least one type of xanthophylles.

14. The method according to claim 13, wherein the type of xanthophyll is astaxanthin.

15. The method according to claim 14, wherein the mammalian gastrointestinal tract is the human stomach and the Helicobacter sp. is *H. pylori*.

16. The method according to claim 14, wherein the xanthophyll is dissolved in an oil of food grade.

17. The method according to claim 14, wherein the astaxanthin is in a form esterified with fatty acids.

18. The method according to claim 17, wherein the astaxanthin derives from a natural source.

19. The method according to claim 18, wherein the natural source is a culture of the alga Haematococcus sp.

20. The method according to claim 14, wherein the oral preparation further comprises carbohydrate structures.

21. The method according to claim 20, wherein the oral preparation comprises algal meal having astaxanthin in esterified form with fatty acids dissolved in small droplets of naturally occurring oil and naturally occurring carbohydrate structures in the partially disrupted algal cell walls.

22. The method according to claim 14, which further comprises administration of a prophylactically effective amount of a water soluble antioxidant.

23. The method according to claim 10, wherein the water soluble antioxidant is ascorbic acid (Vitamin C).

24. The method according to claim 14, wherein the oral preparation is presented in a separate unit dose or in mixture with food.

25. The method according to claim 1, which further comprises administration of a therapeutically effective amount of a water soluble antioxidant.

26. The method according to claim 13, which further comprises administration of a prophylactically effective amount of a water soluble antioxidant.

* * * * *